(12) United States Patent
Gov

(10) Patent No.: US 12,383,757 B2
(45) Date of Patent: Aug. 12, 2025

(54) TIP SECTION FOR USE IN PHOTOTHERAPY

(71) Applicant: STRATA SKIN SCIENCES INC., Horsham, PA (US)

(72) Inventor: Shmuel Gov, Carlsbad, CA (US)

(73) Assignee: STRATA SKIN SCIENCES INC., Horsham, PA (US)

( * ) Notice: Subject to any disclaimer, the term of this patent is extended or adjusted under 35 U.S.C. 154(b) by 466 days.

(21) Appl. No.: 17/634,079

(22) PCT Filed: Aug. 19, 2020

(86) PCT No.: PCT/IL2020/050906
§ 371 (c)(1),
(2) Date: Feb. 9, 2022

(87) PCT Pub. No.: WO2021/038556
PCT Pub. Date: Mar. 4, 2021

(65) Prior Publication Data
US 2022/0288415 A1    Sep. 15, 2022

Related U.S. Application Data

(60) Provisional application No. 62/892,521, filed on Aug. 27, 2019.

(51) Int. Cl.
*A61N 5/06*    (2006.01)
*A61N 5/067*   (2006.01)

(52) U.S. Cl.
CPC .......... *A61N 5/0616* (2013.01); *A61N 5/067* (2021.08); *A61N 2005/0642* (2013.01); *A61N 2005/0661* (2013.01)

(58) Field of Classification Search
CPC ... A61B 18/203; A61B 5/0075; A61B 5/0093; A61B 18/22; A61B 2017/00057;
(Continued)

(56) References Cited

U.S. PATENT DOCUMENTS

| 5,830,164 A | 11/1998 | Cone et al. |
| 2005/0251242 A1* | 11/2005 | Bousfield ............. A61N 5/0617 607/150 |

(Continued)

FOREIGN PATENT DOCUMENTS

DE    102004017547 A1    10/2005

OTHER PUBLICATIONS

Definition of About. Merriam-Webster Dictionary, retrieved on Apr. 1, 2025; Retrieved from the Internet: <https://www.merriam-webster.com/dictionary/about> (Year: 2025).*
(Continued)

*Primary Examiner* — Niketa Patel
*Assistant Examiner* — Sebastian X Lukjan
(74) *Attorney, Agent, or Firm* — Gottlieb, Rackman & Reisman, PC (57) ABSTRACT

A tip section for assembly on a phototherapy apparatus the tip section including a front panel having a proximal surface and a distal surface; and at least two nozzles configured to allow passage of laser radiation therethrough, the at least two nozzles protruding out from a distal surface of the front panel, wherein the at least two nozzles include leading edges at their distal end, that are configured to part hair when combed therethrough; and wherein the at least two nozzles are arranged essentially in parallel one next to another along a major axis thereof.

19 Claims, 5 Drawing Sheets

(58) Field of Classification Search
CPC .... A61B 2018/00684; A61B 2018/00785; A61B
2018/00994; A61B 2018/2035; A61B
2018/20359; A61B 2018/00452; A61B
2018/20353; A61M 37/0092; A61N
5/0616; A61N 5/0067; A61N 5/0622;
A61N 5/062; A61N 5/067; A61N
2005/0642; A61N 2005/0661; A61N
2005/063; A61N 2005/0644
See application file for complete search history.

(56) References Cited

U.S. PATENT DOCUMENTS

| | | | |
|---|---|---|---|
| 2007/0179574 A1* | 8/2007 | Elliott | A61N 5/0616 607/94 |
| 2008/0172112 A1* | 7/2008 | Gourgouliatos | A61N 5/0617 607/94 |
| 2008/0201979 A1 | 8/2008 | Rhoades | |
| 2009/0287195 A1* | 11/2009 | Altshuler | A46B 15/0036 606/9 |
| 2018/0055690 A1* | 3/2018 | Miller | A61F 9/009 |
| 2018/0140867 A1 | 5/2018 | Levatter et al. | |

OTHER PUBLICATIONS

PCT International Search Report for International Application No. PCT/IL2020/050906, mailed Nov. 29, 2020, 3pp.
PCT Written Opinion for International Application No. PCT/IL2020/050906, mailed Nov. 29, 2020, 7pp.

* cited by examiner

TIP SECTION FOR USE IN PHOTOTHERAPY

This application is a National Phase of PCT Patent Application No. PCT/IL2020/050906 having International filing date of Aug. 19, 2020, which claims the benefit of priority of U.S. Provisional Patent Application No. 62/892,521, filed Aug. 27, 2019, the contents of which are all incorporated herein by reference in their entirety.

TECHNICAL FIELD

This disclosure relates to devices, parts thereof and a method of using same for phototherapy treatments of skin diseases, preferably skin diseases located on the scalp and other parts of the body covered by hair.

BACKGROUND

Inflammatory diseases of the skin affect a large portion of the population. Psoriasis, for example, affects about 2%-3% of the world's population. Psoriasis involves an abnormally fast rate of cell proliferation in the basal layer of the epidermis giving rise to red, scaly plaques and bleeding when traumatized. Past methods of treatment of skin psoriasis include the application of tars, salicylic acid, steroids, ultraviolet light (phototherapy), and a combination of ultraviolet light with photoactive compounds (photochemotherapy).

Phototherapy involves UV irradiation of the affected area. For example, psoriasis has been treated with ultraviolet-B (UV-B) light having wavelengths from 290-320 nm. Other skin diseases which have been treated successfully with ultraviolet light include eczema, mycosis fungicides, and lichen planus. In addition, ultraviolet light may have a role in the treatment of seborrheic dermatitis.

Xenon Chloride (XeCl) excimer lasers, producing ultraviolet (UV) light energy within the B range (290-320 nm) of the electro-magnetic spectrum, have been used to provide phototherapy for specific dermatological disorders.

However, utilizing such devices for administering phototherapy treatment to the scalp is difficult and time consuming for patients who are not bald. The current treatment devices require using a comb to part the hair over the affected area, at times holding the hair with fingers and/or clips to keep it out of the way, and only then administering phototherapy.

Therefore, a need exists for a device which can provides scalp treatment without the need for repeated parting and clipping.

SUMMARY OF THE INVENTION

Aspects of the disclosure, in some embodiments thereof, relate to devices, parts thereof and a method of using same for phototherapy treatments of skin diseases, preferably skin diseases located on the scalp and other parts of the body covered by hair, such as, but not limited to, psoriasis.

According to some embodiments, the device is a tip section configured to be assembled on a handpiece of a laser emitting device to allow phototherapy treatment of a non-bald subject's scalp without requiring manual parting with fingers and/or clips of the subject's hair prior to providing the treatment, thus enabling using only one hand for providing the phototherapy treatment.

According to some embodiments, the device includes a front panel having a proximal surface and a distal surface; and at least two nozzles protruding out from the distal surface of the front panel and having leading edges configured to part hair, and expose the scalp, when combed therethrough. Advantageously, the device thus makes treating easier and faster without the need for repeated parting and clipping and is particularly beneficial for subjects having short hair, which cannot be clipped out of the way of the light source.

According to some embodiments, the nozzles are arranged essentially in parallel on the front panel, one next to another along a major axis thereof. Advantageously, the space between two neighboring nozzles may be smaller at their distal end than at their center portion, thereby forming a funnel capable of retaining therein the hair that has been parted by the leading edges of the nozzles.

As a further advantage, the laser radiation passes through the nozzles and reflects off the walls of the nozzles thus directly and indirectly illuminating the scalp. This advantageously obviates the need for the laser radiation to be transmitted through optical fibers that attenuate the UV radiation that could be easily damaged by the high energy densities provided by the laser and which may easily break. Furthermore, the efficient illumination due to the high doses and power allowed by the direct and indirect transmission, the large area covered in a single dose, and the ability to provide continuous treatment using a single hand, will expedite treatment times.

According to some embodiments, there is provided a tip section for assembly on a phototherapy apparatus, the tip section including: a front panel having a proximal surface and a distal surface; and at least two nozzles configured to allow passage of laser radiation therethrough, the at least two nozzles protruding out from the distal surface of the front panel, wherein the at least two nozzles have leading edges at their distal end, configured to part hair when combed therethrough; and wherein the at least two nozzles are arranged essentially in parallel one next to another along a major axis thereof.

According to some embodiments, at least two nozzles have an elliptical/oval cross-section.

According to some embodiments. at least two nozzles are tapered toward their center such that the cross-sectional areas of the at least two nozzles are larger at their proximal and distal ends than at a center portion thereof. According to some embodiments, the at least two nozzles are tapered such that the cross-sectional areas of the at least two nozzles are larger at their distal ends than at their proximal ends. According to some embodiments, the angle of the taper of the nozzle is 10 to 30 degrees relative to the vertical axis thereof.

According to some embodiments, the space between two neighboring nozzles is smaller at its distal end than at its center portion, thereby forming a funnel configured to retain the hair, parted by the leading edges of the nozzles. According to some embodiments, the space between two neighboring nozzles is smaller at its proximal end than at a center portion thereof such that hair parted by the leading edges of the nozzles gets trapped when reaching a proximal end of the space.

According to some embodiments, the at least two nozzles have a shape of a flattened/squeezed hourglass.

According to some embodiments, the proximal ends of the at least two nozzles are essentially coterminous with the proximal surface of the front panel. As used herein the term "essentially coterminous" refers to the proximal end of the nozzles protruding out from the lower surface of the front panel by less than 2 mm, less than 1 mm, less than 0.5 mm or less than 0.1 mm. Each possibility is a separate embodiment.

According to some embodiments, the cross-sectional area of the distal end opening of each of (or at least sonic of) the at least two nozzles is in the range of 0.5-2 cm$^2$, 0.75-1.75 cm$^2$ or 1.0-1.5 cm$^2$. Each possibility is a separate embodiment.

According to some embodiments, the walls of the at least two nozzles are substantially reflective to ultraviolet light.

According to some embodiments, the at least two nozzles are made of a biocompatible material suitable for injection molding.

According to some embodiments, the front panel and the at least two nozzles are integrally formed as a single unit.

According to some embodiments, there is provided a phototherapy device including: a tip section comprising: a front panel having a proximal surface and a distal surface, as essentially described herein; and at least two nozzles configured to allow passage of laser radiation therethrough, the at least two nozzles protruding out from the distal surface of the front panel, and a base unit configured to receive the front panel of the tip section.

According to some embodiments, the at least two nozzles have leading edges at their distal end, the leading edges configured to part hair when combed therethrough; and According to some embodiments, the at least two nozzles are arranged essentially in parallel, one next to another, along a major axis thereof.

According to some embodiments, the at least two nozzles have an elliptical/oval cross-section.

According to some embodiments, the phototherapy apparatus further includes a laser source, wherein the base unit is attached to a distal end of the laser source.

According to some embodiments, the laser source is configured to emit laser radiation having a wavelength of 308 nm.

According to some embodiments, the laser source is a 308 nm XeCl excimer laser with multiple repetition rates and output doses in the range of 50-9000 mJ/cm$^2$, in the range of 100-5000 mJ/cm$^2$, in the range of 200-2000 mJ/cm$^2$ or in the range of 250-1000 mJ/cm$^2$. Each possibility is a separate embodiment.

According to some embodiments, there is provided a method of treating an area of a scalp affected by a skin disease, the method comprising: providing an effective dose of treatment light to the affected area from a phototherapy device, such as the herein disclosed phototherapy device, wherein providing the treatment comprises combing the subject's hair with the tip section, such that the subject's hair is parted by the leading edges of the nozzles; and transmitting laser radiation from the laser source, through the at least two nozzles, to the part of the subject's scalp exposed by the parting of the subject's hair.

According to some embodiments, the phototherapy device includes: a tip section comprised of a base unit configured to receive the front panel of the tip section; and a laser source.

According to some embodiments, the tip section comprises a front panel having a proximal surface and a distal surface; and at least two nozzles configured to allow passage of laser radiation therethrough, the at least two nozzles protruding out from the distal surface of the front panel. According to some embodiments, the at least two nozzles comprise leading edges at their distal end, said leading edges configured to part hair when combed therethrough. According to some embodiments, the at least two nozzles are arranged essentially in parallel one next to another along a major axis thereof.

According to some embodiments, the space between two neighboring nozzles is smaller at its distal end than at a center portion thereof, thereby forming a funnel configured to retain the hair, parted by the leading edges of the nozzles, and wherein the treatment further comprises catching/retaining the part of the subject's hair parted by the leading edges in the funnel.

According to some embodiments, the treatment light has a wavelength of 308 nm.

According to some embodiments, the skin disease is scalp psoriasis.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Reference is now made to FIG. 1A-FIG. 1F, which show different views of a tip section 100 for assembly on a phototherapy apparatus, according to some embodiments. Tip section 100 includes a front panel 110 comprising an inner panel 114 configured to be received within a base unit, such as base unit 200 shown in FIG. 2A and FIG. 2B, herein below, and an outer panel 112 configured to lie against frame 212 of base unit 200.

Tip section 100 further includes nozzles 120 configured to allow passage of laser radiation therethrough as well as by reflections off the walls of the nozzles. Tip section 100 is here shown to include three nozzles but may include a different number of nozzles such as 2, 4, 5 or more nozzles. Each possibility is a separate embodiment. As best seen from FIG. 1A, a distal end of nozzles 120 protrude out from outer panel 112 of front panel 110 While a proximal end of nozzles 120 is essentially coterminous with the surface of the inner panel 114 of front panel 110.

According to some embodiments, tip section 100 may have an elliptical, oval, rectangular or other cross-section forming a comb-like structure suitable for parting hair, when combed therethrough. According to some embodiments, nozzles 120 are arranged essentially in parallel one next to another along their major axis thereof, such that each nozzle can part hair when combed through the hair, minor axis first.

According to some embodiments, two neighboring nozzles 120 may be spaced apart by 0.1-0.8 cm or 0.1-0.5 cm at their distal end, such as, but not limited to, 0.33 cm. As seen in FIG. 1F, the space 132 between two neighboring nozzles may be narrower at its proximal end than at its distal end, such that hair, entering space 132 as a result of the parting, gets trapped and thus retained within space 132. Additionally or alternatively, space 132 between two neighboring nozzles 120 may be narrower at its distal end than at a central portion thereof, thereby forming a funnel/channel within which hair, parted during combing is retained. It is understood that other configurations providing the advantageous retaining of parted hair within space 132 is also envisaged and, as such, a part of this disclosure.

According to some embodiments, the distal end of at least some (preferably all) of nozzles 120 include a leading edge 124 configured to ease the parting of the hair, when combed therethrough.

According to some embodiments, tip section 100 may have a shape of a flattened tube. According to some embodiments, tip section 100 may have a shape of a flattened hourglass, i.e. being tapered toward the center portion 126 thereof (forming a "waist"), such that the cross-sectional areas of nozzles 120 are larger at their proximal end and distal end than at a center portion 126 thereof. According to some embodiments, nozzles 120 may be tapered only from the distal end of nozzles 120 towards central portion 126 thereof, whereas the portion of nozzles 120 extending from the proximal end toward center portion 126 is essentially non-tapered (option not shown). such that the cross-sectional areas of the nozzles 120 are larger at their distal end than at their proximal end.

According to some embodiments, the taper at a lateral side 128 of nozzles 120 may be different than a taper at a frontal side 129 of nozzles 120. As a nonlimiting example, the taper at lateral side 128 of nozzles 120 may be such that the minor axis at the proximal end of nozzles 120 is larger than the minor axis at the distal end of nozzles 120, whereas the taper at frontal side 129 of nozzles 120 may be such that the major axis at distal end of nozzles 120 is larger than the major axis at the proximal end of nozzles 120.

As used herein, the term "tapered" toward a central portion refers to the wall of nozzles 120 having an angle α (alpha) and/or β (beta) which are/is less than 90° (degrees). According to some embodiments, the angles α (alpha) and β (beta) may be essentially identical (e.g. different due only to tolerance). According to some embodiments, the angles α (alpha) and β (beta) may be different for example, the angle α (alpha) may be larger than the angle β (beta) such that the taper from the proximal end toward the central portion is larger than that of the taper from the distal end toward the central portion. According to some embodiments, the angle α (alpha) may be smaller than the angle β (beta) such that the taper from the distal end of the nozzle toward the central portion is larger than that of the taper from the proximal end toward the central portion.

As used herein, the term "non-tapered" refers to the wall of nozzles 120 having an angle α (alpha) and/or β (beta) which is 90° (degrees)±5 degrees (e.g. due to tolerances of production).

Figure 1A:
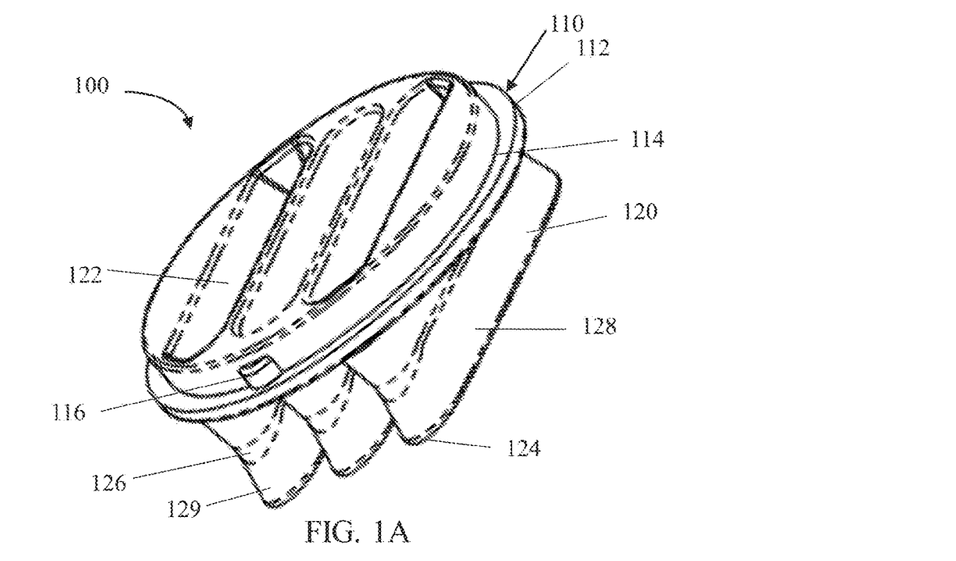
FIG. 1A is a bottom perspective view of a tip section for assembly on a phototherapy apparatus, according to some embodiments.
Figure 1B:
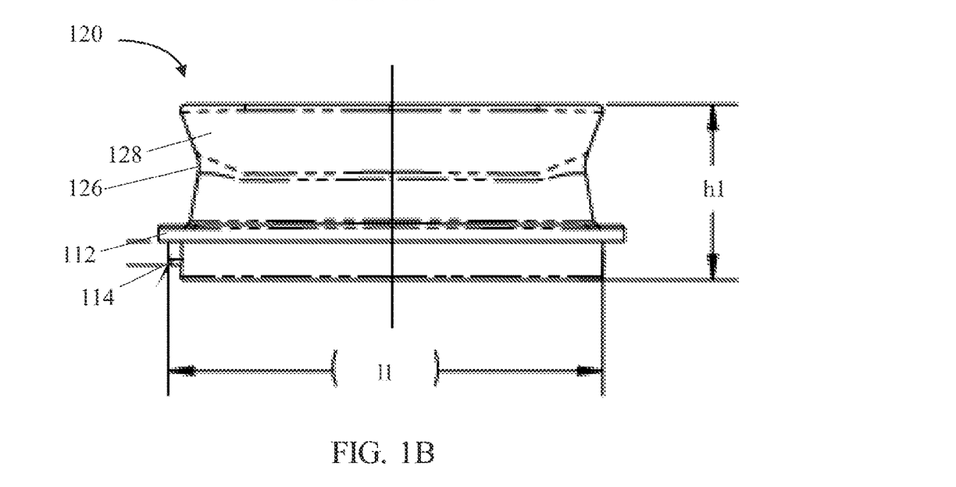
FIG. 1B is a side view of the tip section of FIG. 1A, showing a lateral side of its nozzles, according; to some embodiments.
Figure 1C:
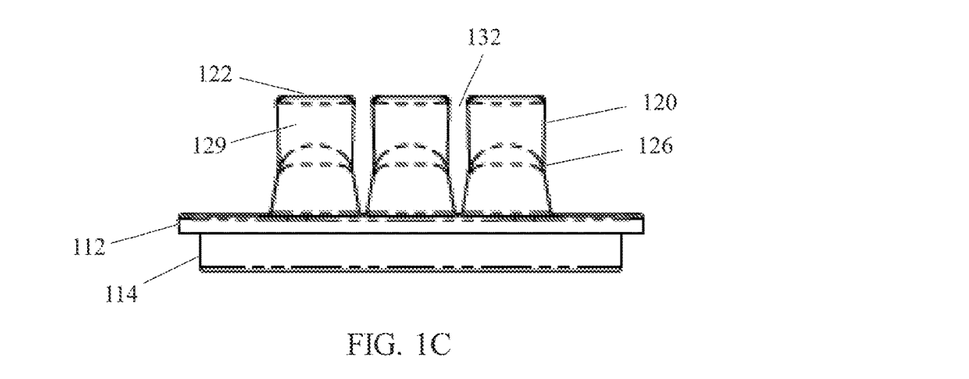
FIG. 1C is a side view of the tip section of FIG. 1A showing a frontal side of its nozzles, according to some embodiments.
Figure 1D:
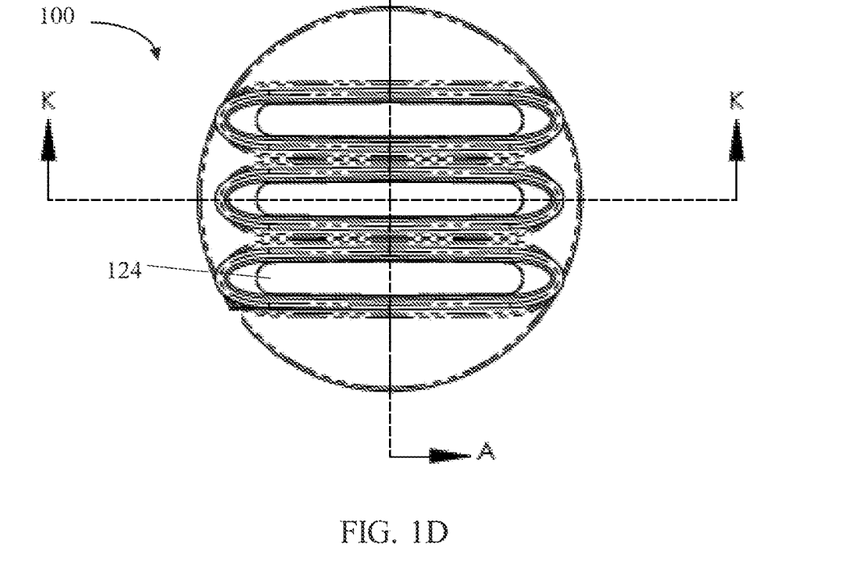
FIG. 1D is a top view of the tip section of FIG. 1A, according to some embodiments.

As seen in FIG. 1B, the height h1 of tip section 100 may be in the range of 0.5-3.5 cm, 0.7-2 cm or 1.0-1.5 cm such as, but not limited to, about 1.3 cm. As a non-limiting example, the height h1 of tip section 100 may be about 1.17 cm.

Similarly, the length l1 of tip section 100 may be in the range of 2.0-4.0 cm, 2.3-3.8 cm or 2.5-3.0 cm, such as, but not limited to, about 2.8 cm. As a non-limiting example, the length l1 of tip section 100 may be about 2.9 cm.

Figure 1E:
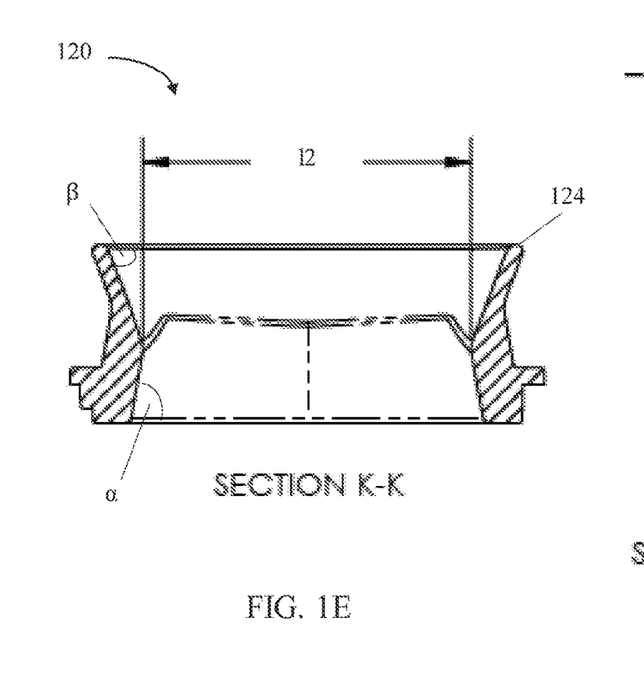
FIG. 1E is a cross sectional view of FIG. 1A along the line K-K depicted in FIG. 1D, according to some embodiments.
Figure 1F:
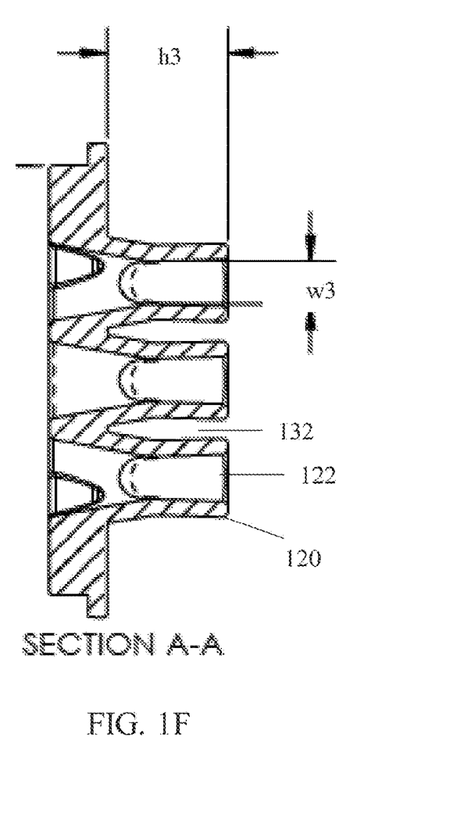
FIG. 1F is a cross sectional view of FIG. 1A along the line A-A depicted in FIG. 1D, according to some embodiments.

As seen in FIG. 1E, nozzles 120 may have a length l2 in the range of 1.0-3.0 cm, 1.2-2.7 cm or 1.5-2.5 cm, such as, but not limited to, about 2.13 cm, as measured at their distal end.

As seen in FIG. 1F, nozzles 120 may have a width w3 in the range of 0.1-1 cm, 0.1-0.5 cm or 0.2-0.4 cm such as, but not limited to, about 0.25 cm (e.g. 0.28 cm), as measured at their distal end.

According to some embodiments, the distal end opening 122 of each of nozzles 120 may have a cross sectional area of 0.3-2.0 square centimeter ($cm^2$), such as, but not limited to, about 0.63 $cm^2$. It is thus understood that tip section 100 is capable of providing phototherapy treatment to an area of 3×0.63 $cm^2$ in a single dose in an essentially uniform manner as compared to phototherapy treatment provided through a plurality of optic fibers, which together may cover a large area, but which cannot provide a uniform treatment to the area in a single shot. Tip section 100 is very robust in terms of ability to deliver the same energy between doses due to its material composition compared to a treatment using optical fibers that could be easily damaged or cause a reduction in energy from the bending of each individual optical fiber. It would also be much more difficult to clean these optical fibers compared to assembled base 200 and tip section 100, which can be dipped in a high level disinfectant and reused. The overall treatment with a light source, such as but not limited to a 308 nm laser and assembled base unit 200 and tip section 100 would likely allow for faster treatment time at higher dose levels compared to a lamp at a similar wavelength using optical fibers.

According to some embodiments, the walls of nozzles 120 are substantially reflective to ultraviolet light, thus ensuring efficient delivery of the laser radiation and consequently of the phototherapy. According to some embodiments, nozzles 120 may be made of any biocompatible (ISO 10993) material that can be injection molded, such as, but not limited to, a polycarbonate material (e.g. Lexan 141). According to some embodiments, nozzles 120 and front panel 110 may be made of a same material. According to some embodiments, nozzles 120 and front panel 110 may be made of a different material.

According to some embodiments, front panel 110 and nozzles 120 may be integrally formed as a single unit, for example as a single mold. Alternatively, front panel 110 and nozzles 120 may be formed separately and subsequently be assembled into a single unit.

Figure 2A:
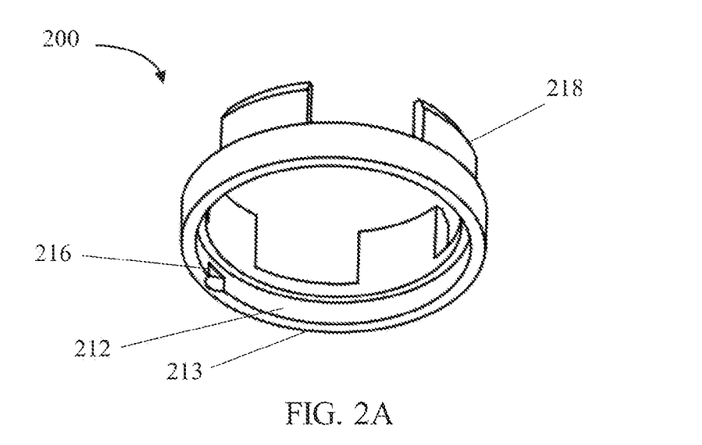
FIG. 2A is a bottom perspective view of a base unit configured to receive the front panel of the tip section of FIG. 1A, according to some embodiments.
Figure 2B:
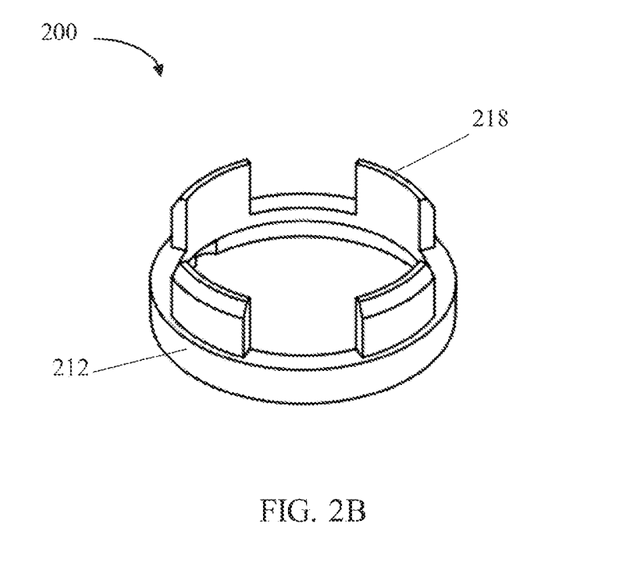
FIG. 2B is a top perspective view of the base unit of FIG. 2 according to some embodiments.

Reference is now made to FIG. 2A and FIG. 2B, which show different views of a base unit 200 attached to, configured to be assembled on or which is attachable to a distal end of a laser emitting/transmitting element, as further elaborated hereinbelow. Base unit 200 includes a frame 212 configured to receive, encompass, encage and or enclose inner panel 114 of tip section 100, such that outer panel 112 of tip section 100 will lie against and align rim 213 of base unit 200. Once inserted, tip section 100 is secured due to a mechanical fastening mechanism, such as, but not limited to, a press fit mechanism including interacting elements positioned on an outer surface of inner panel 114 of tip section 100 and on an inner surface of frame 212 of base unit 200, here illustrated as a locating boss 116 which is configured to be received within notch 216, respectively. Alternatively, in some embodiments, base unit 200 and tip section 100 may be inseparable, i.e. represent a single piece of injection-molded plastic.

Frame 212 of base unit 200 further includes connecting/fitting elements 218 configured to attach base unit 200 to the distal end of the laser emitting/transmitting element.

Figure 3A:
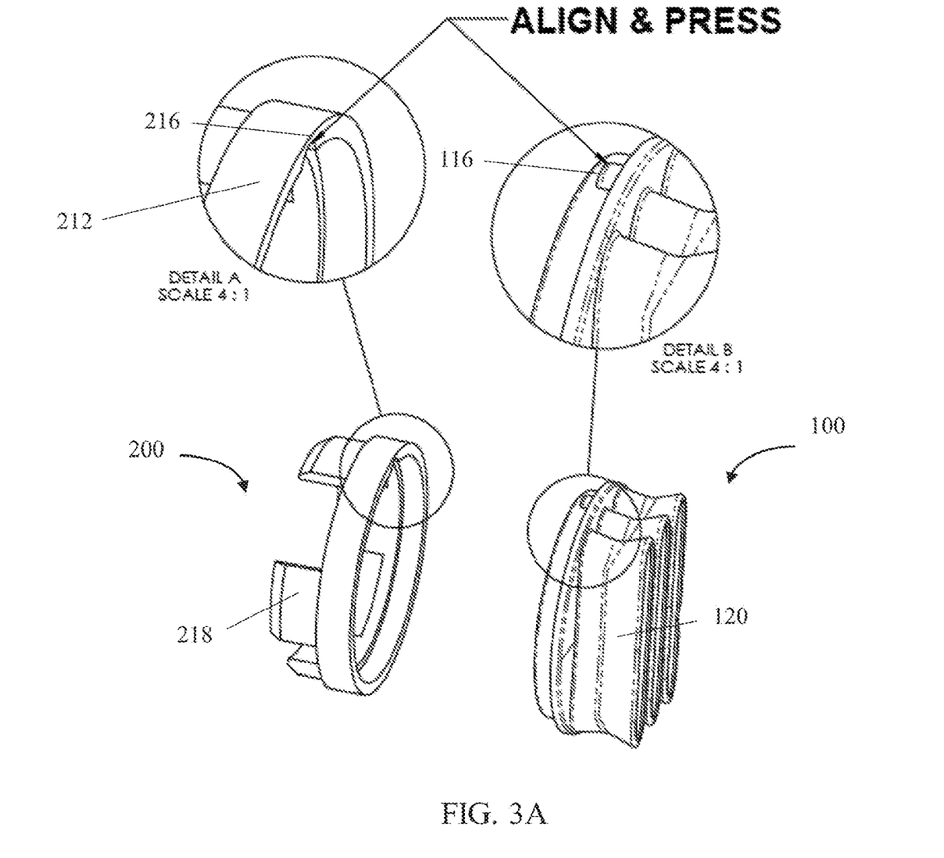
FIG. 3A is a perspective view of the assembly of the tip section of FIG. 1A-FIG. 1F with the base unit of FIG. 2A and 2B, according to some embodiments.
Figure 3B:
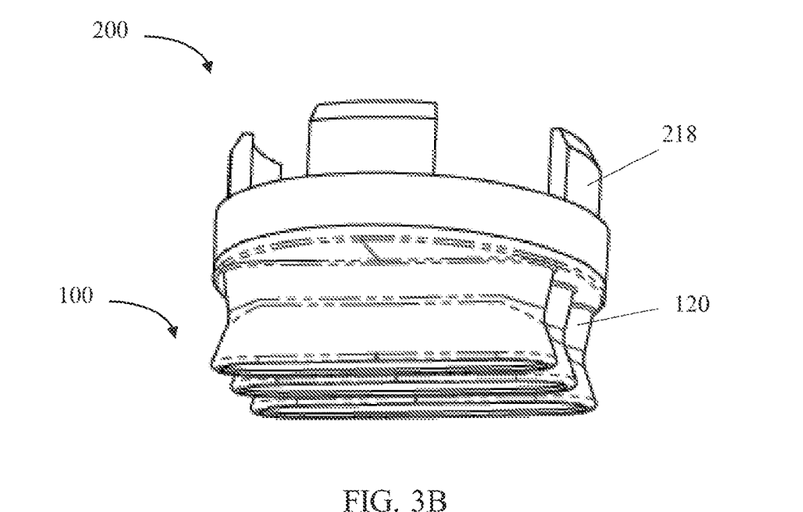
FIG. 3B is a side view of the tip section of FIG. 1A-FIG. 1F after assembly to the base unit of FIG. 2A and 2B; according to some embodiments

Reference is now made to FIG. 3A and FIG. 3B, which show the assembly of tip section 100 to base unit 200; according to some embodiments. As seen in the enlargements, frame 212 of base unit 200 includes a notch 216 configured to receive the locating boss 116 of tip section 100 thereby interlocking and aligning tip section 100 to base unit 200. Once assembled, the assembly may be attached to a handpiece through connecting/fitting elements 218. Alternatively, base unit 200 may initially be attached to a handpiece, whereafter tip section 100 is attached to base unit 200.

Figure 4A:
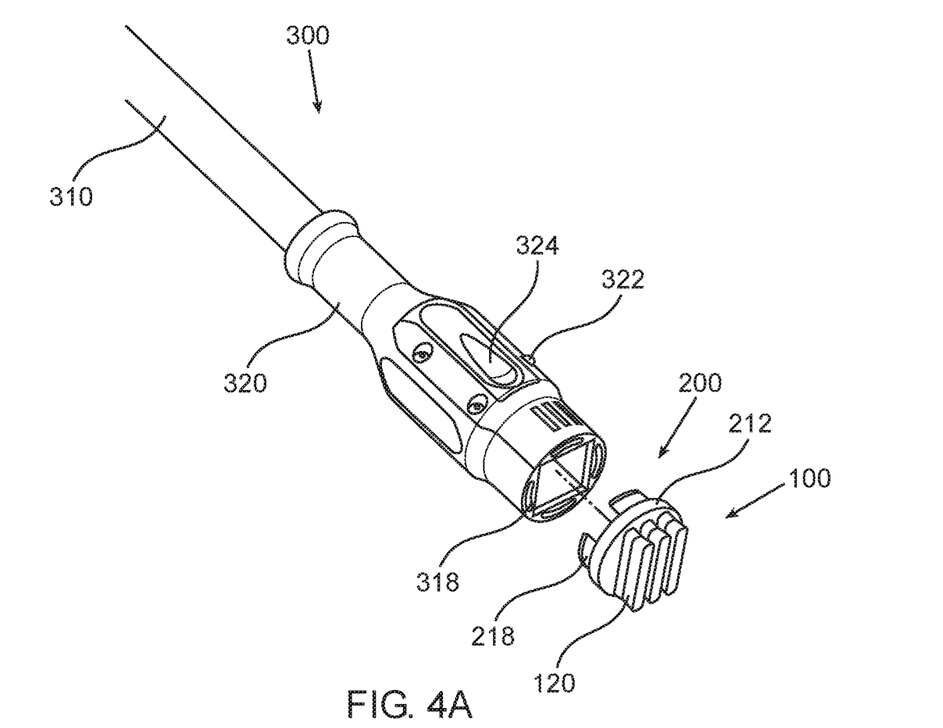
FIG. 4A is a perspective view of a laser handpiece during assembly with the base unit-tip section assembly illustrated in FIG. 3B. according to some embodiments.
Figure 4B:
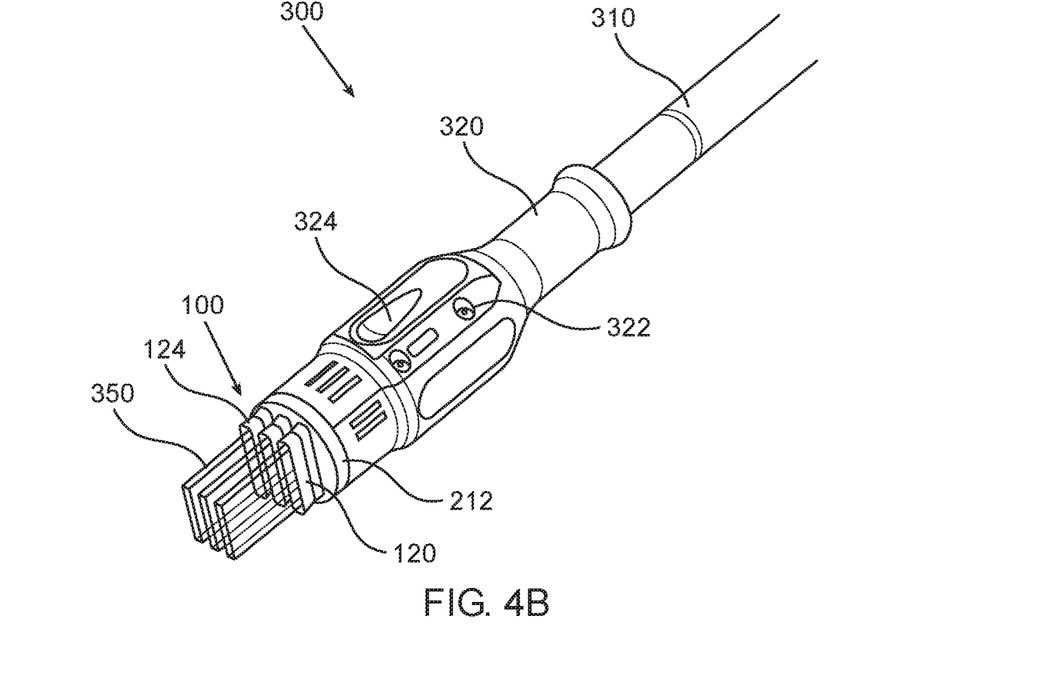
FIG. 4B is a perspective view of a laser handpiece assembled with the base unit-tip section assembly of FIG. 3B.

Reference is now made to FIG. 4A and FIG. 4B, which show perspective views of a laser handpiece 300 during and after attachment with the assembly of base unit 200 of FIG. 2A and FIG. 2B and tip section 100 illustrated in FIG. 3B, according to some embodiments. Laser handpiece 300 is connected or connectable to a laser, such as, but not limited to, an XeCl excimer laser with an output in the range of 290 nm-320 nm, e.g. 308 nanometer, via a fiber optic cable 310 which terminates with a handpiece grip 320 configured for gripping by a user. According to some embodiments, fiber optic cable 310 includes a flexible, liquid fiber-optic (Light Liquid Guide or LLG). The body of the handpiece includes control buttons, such as 322 (control switch) and 324 (safety lever) configured to control parameters of the phototherapy. As best seen in FIG. 4A, the distal end of laser handpiece 300 is configured to be assembled with a base unit, such as, but not limited to, base unit 200 via insertion of connecting/fitting elements 218 into matching receptacles 318. According to some alternative embodiments, base unit 200 may be initially assembled onto handpiece 300, whereafter a tip section, such as tip section 100 may be attached to base unit 200, as essentially described herein.

According to some embodiments, the laser radiation has a wavelength of 290-320 nm. According to some embodiments, the laser radiation has a wavelength of 308 nm. Upon full assembly, laser radiation 350 may be provided through nozzles 120. According to some embodiments, the dose of the laser radiation may be in the range of 50 mJ/cm$^2$-9,000 mJ/cm$^2$. According to some embodiments, the laser radiation has a pulse repetition rate of up to 1200 Hz, such as, but not limited to, 250 Hz, 400 Hz or 1000 Hz. According to some embodiments, the laser radiation has a beam size at delivery (from each nozzle) within the range of 0.5 cm2-2 cm$^2$, such as, but not limited to, 0.63 cm2 According to some embodiments, the laser radiation has a nominal operating fluence per pulse of 2.0 mJ/cm$^2$-4.5 mJ/cm$^2$, such as, but not limited to, 3.8 mJ/cm$^2$.

According to some embodiments, handpiece 300 is further configured to deliver an aiming beam. According to some embodiments, the aiming beam may have a wavelength in the visible light spectrum. According to some embodiments, the aiming beam may be green light. According to some embodiments, the aiming beam may have a wavelength of 532 nm. According to some embodiments, the aiming beam is a low power 532 nm (green) diode laser that aides proper positioning of the therapeutic UVB beam prior to delivering the actual dose.

According to some embodiments, handpiece 300 assembled with tip section 100 and base unit 200 may be particularly suitable for providing phototherapy to skin diseases located on the scalp and other parts of the body covered by hair. According to some embodiments, handpiece 300 assembled with tip section 100 and base unit 200 may be suitable for providing phototherapy to subjects suffering from scalp psoriasis. According to some embodiments, handpiece 300 assembled with tip section 100 and base unit 200 may be suitable for providing phototherapy to non-bald subjects. According to some embodiments, handpiece 300 assembled with tip section 100 and base unit 200 may be suitable for providing phototherapy to subjects with short to mid-length hair. According to some embodiments, handpiece 300 assembled with tip section 100 may be particularly advantageous when providing phototherapy to subjects with short hair which cannot be clipped out of the way of the light source.

According to some embodiments, there is provided a method for treating scalp psoriasis, the method including providing laser treatment to a subject's scalp utilizing a handpiece, such as, but not limited to, handpiece 300, assembled with tip section 100 and base unit 200. According to some embodiments, the treatment comprises providing 308 nm laser radiation to the subject's scalp via nozzles 120 of tip section 100. According to some embodiments, providing the treatment comprises combing nozzles 120 through the subject's hair, such that leading edges 124 of nozzles 120 part the subject's hair to expose part of the scalp prior to or along with the providing of the laser radiation. According to some embodiments, parting of the subject's hair may further include retaining the parted hair within space 132 between neighboring nozzles. According to some embodiments, the laser radiation may be provided continuously during combing of the subject's hair. Alternatively the laser radiation may be provided sequentially, e.g. laser radiation may be provided to a first exposed area, upon completion of the treatment to the first area, the laser radiation is halted, the handpiece moved such that a second area is exposed by the combing of nozzles 120 and only then the laser retreatment is reinitiated so as to treat the second area. According to some embodiments, providing the treatment comprises providing the 308 nm laser radiation at a pulse repetition rate of up to 1200 Hz. According to some embodiments, providing the treatment comprises providing the 308 nm laser radiation at a dose of 50 mJ/cm$^2$-9,000 mJ/cm$^2$. According to some embodiments, providing the treatment comprises providing a single dose of laser radiation to an area of the subject's scalp in the range of 1 cm$^2$-4 cm$^2$, or in the range of 0.5 cm$^2$-2 cm$^2$ for a single nozzle.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What I claim is:

1. A tip section configured to be assembled on a distal end of a phototherapy apparatus, the tip section comprising:
    a front panel having a proximal surface and a distal surface; and
    at least two nozzles configured to allow passage of laser radiation therethrough protruding out from the distal surface of the front panel,
    wherein each of the at least two nozzles comprise a leading edge at a distal end of each of the at least two nozzles that is configured to part hair when combed therethrough,
    wherein the at least two nozzles extend longitudinally about the front panel and are arranged in parallel to each other; and
    wherein the at least two nozzles are each tapered toward a center portion such that a cross-sectional area of each of the at least two nozzles is larger at a proximal end and a distal end of each of the at least two nozzles than at the center portion of each of the at least two nozzles.

2. The tip section of claim 1, wherein the at least two nozzles each have an elliptical/oval cross-section.

3. The tip section of claim 1, wherein the at least two nozzles are each tapered such that a cross-sectional area of each of the at least two nozzles is larger at a distal end than at a proximal end of each of the at least two nozzles.

4. The tip section of claim 1, wherein the at least two nozzles are each tapered with an angle of a taper of each of the at least two nozzles being 10 to 30 degrees relative to a vertical axis of each of the at least two nozzles.

5. The tip section of claim 1, wherein a space between two neighboring nozzles of the at least two nozzles is smaller at a distal end of each the at least two nozzles than at a center portion of each of the at least two nozzles thereby forming a funnel configured to retain the hair, parted by the leading edge of each of the at least two nozzles.

6. The tip section of claim 1, wherein a space between two neighboring nozzles of the at least two of the nozzles is smaller at a proximal end of each of the at least two nozzles than at a center portion of each of the at least two nozzles such that the hair parted by the leading edges of each of the at least two nozzles gets trapped when reaching a proximal end of the space.

7. The tip section of claim 1, wherein the at least two nozzles each have a shape of a flattened/squeezed hourglass.

8. The tip section of claim 1, wherein a proximal end of each the at least two nozzles is coterminous with the proximal surface of the front panel.

9. The tip section of claim 1, wherein a cross-sectional area of a distal end opening of each of the at least two nozzles is in a range of 0.5-2 cm$^2$.

10. The tip section of claim 1, wherein the at least two nozzles each include walls that are reflective to ultraviolet light.

11. The tip section of claim 1, wherein the at least two nozzles are made of biocompatible material suitable for injection molding.

12. The tip section of claim 1, wherein the front panel and the at least two nozzles are integrally formed as a single unit.

13. A phototherapy device, comprising:
    a tip section including a front panel having a proximal surface and a distal surface configured to be arranged on a distal end of the phototherapy device; and
    at least two nozzles configured to allow passage of laser radiation therethrough protruding from the distal surface of the front panel, the at least two nozzles each having leading edges at a distal end, said leading edges configured to part hair when combed therethrough, the at least two nozzles which extend longitudinally, arranged in parallel one next to another, and wherein the at least two nozzles are each tapered toward a center portion such that a cross-sectional area of each of the at least two nozzles is larger at a proximal end and a distal end of each of the at least two nozzles than at the center portion of each of the at least two nozzles; and
    a base unit configured to receive the front panel of the tip section.

14. The phototherapy apparatus of claim 13, wherein the at least two nozzles each have an elliptical/oval cross-section.

15. The phototherapy apparatus of claim 13, further comprising a laser source configured to emit laser radiation having a wavelength of 308 nm, wherein the base unit is attached to a distal end of the laser source.

16. A method of treating an area of a scalp affected by a skin disease, the method comprising the following steps:
    providing a tip section comprising a front panel having a proximal surface, a distal surface and at least two nozzles, the at least two nozzles extend from the distal surface of the front panel, extend in parallel longitudinally about the front panel and are configured to allow passage of laser radiation therethrough, the at least two nozzles are each tapered toward a center portion such that a cross-sectional area of each of the at least two nozzles is larger at a proximal end and a distal end of each of the at least two nozzles than at the center portion of each of the at least two nozzles and at a distal end of the at least two nozzles each of the at least two nozzles comprise a leading edge said leading that is configured to part hair when combed therethrough;
    providing a phototherapy device configured to transmit laser light;
    arranging the tip section on a distal end of the phototherapy device;
    combing the hair with the tip section, such that the hair is parted by the leading edge of each of the at least two nozzles; and
    transmitting a dose of laser light from the phototherapy device, through the at least two nozzles, to a portion of the scalp affected by the skin disease and exposed by parting of the hair.

17. The method of claim 16, wherein a space between the two nozzles is smaller at a distal end than at a center portion of each of the at least two nozzles thereby forming a funnel configured to retain the hair, parted by the leading edge of each of the nozzles, and wherein the treatment further comprises catching/retaining the part of the hair parted by the leading edge of each of the two nozzles in the funnel.

18. The method of claim 16, wherein the laser light has a wavelength of 308 nm.

19. The method of claim 16, wherein the skin disease is scalp psoriasis.

\* \* \* \* \*